United States Patent [19]

Matsumura

[11] 4,318,585
[45] Mar. 9, 1982

[54] OPTICAL SYSTEM WITH AN AFOCAL FOCUSING GROUP

[75] Inventor: Isao Matsumura, Yokosuka, Japan

[73] Assignee: Canon Kabushiki Kaisha, Tokyo, Japan

[21] Appl. No.: 65,004

[22] Filed: Aug. 8, 1979

[30] Foreign Application Priority Data

Aug. 15, 1978 [JP] Japan .................. 53-99365

[51] Int. Cl.$^3$ .................. A61B 3/12; G02B 27/40
[52] U.S. Cl. .................. 350/46; 350/453; 351/7; 351/14
[58] Field of Search .................. 350/46, 47, 54, 453; 351/7, 16, 14

[56] References Cited

U.S. PATENT DOCUMENTS 3,259,039  7/1966  Okajima .................. 350/54 X

Primary Examiner—John K. Corbin
Assistant Examiner—M. Koren
Attorney, Agent, or Firm—Toren, McGeady & Stanger

[57] ABSTRACT

The present invention refers to an optical system consisting of an objective lens, an aperture stop, a fixed lens and a movable lens group, whereby the aperture stop corresponds to the primary focal plane of the fixed lens group so that the pupil through which the light beam emerges is formed at the infinite distance. The movable lens group consists of two lenses whose focal planes correspond to each other and even if the movable lens group is moved along, the direction of the optical axis for focusing the position and the dimension of the pupil of the optical system do not change.

13 Claims, 7 Drawing Figures

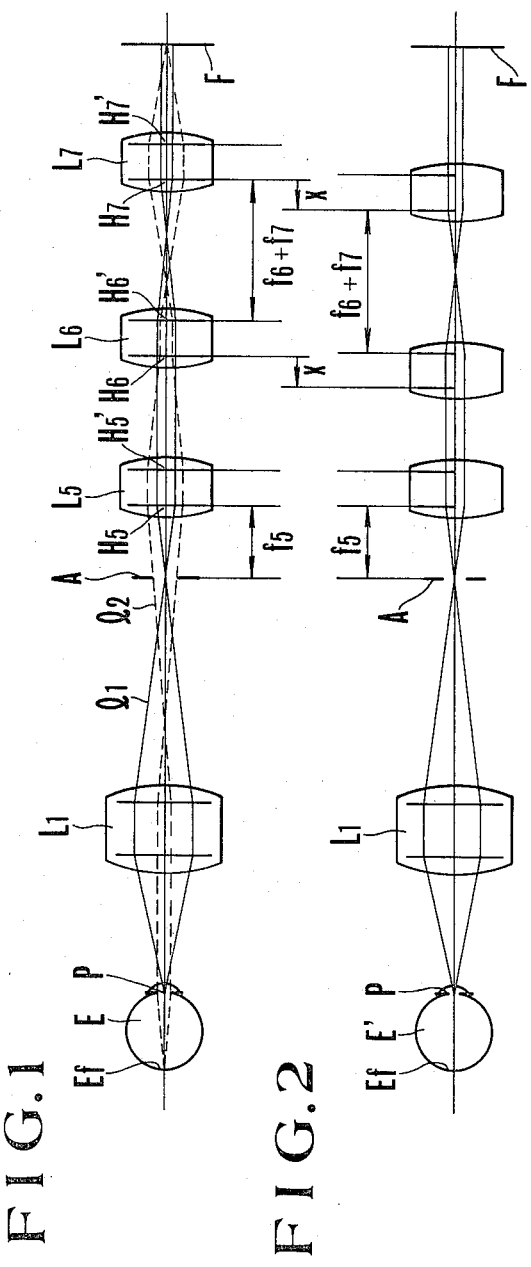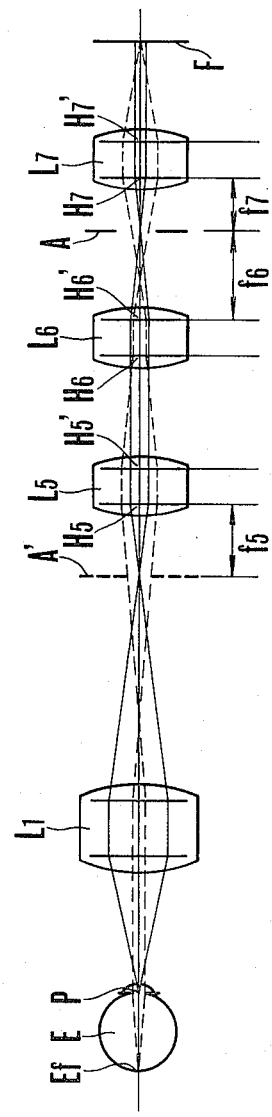
FIG.1  FIG.2  FIG.3

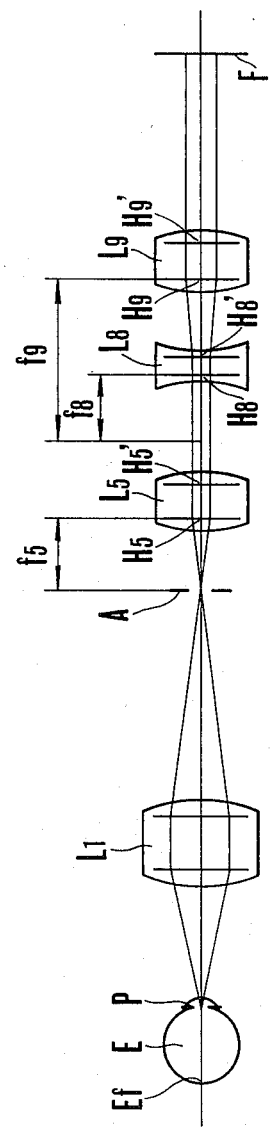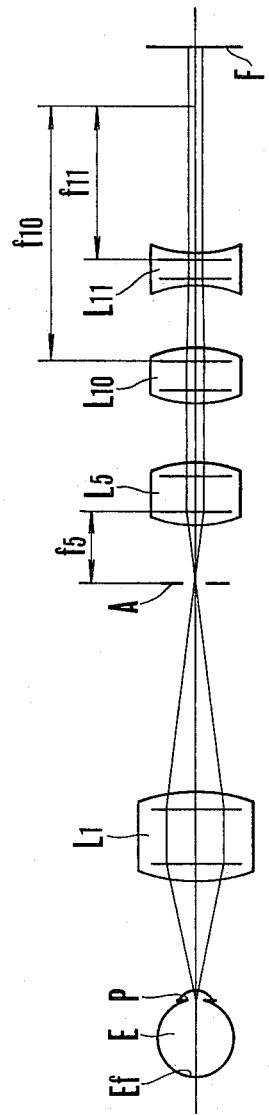

OPTICAL SYSTEM WITH AN AFOCAL FOCUSING GROUP

BACKGROUND OF THE INVENTION

The present invention relates to an optical system for focusing by moving a part of the optical members, which system is particularly capable of focusing without changing the size of the pupil of the optical system.

Generally, the entire lens or a part of the elements are moved along the direction of the optical axis for focusing the object by means of the photographing lens, whereby in order to focus the eye fundus with an ophthalmic investigation instrument such an as eye fundus camera or ophthalmic refractometer, the photographing film or a part of the image forming optical system is moved.

Below, the problems accompanied with the focusing will be explained in accordance with an ophthalmic investigation instrument having many such difficulties.

FIGS. 6 and 7 respectively show a conventional focusing method for ophthalmic instruments. In FIG. 6, E is the eye to be inspected, Ef is the eye fundus, P is the pupil, $L_1$ is the objective lens and $L_2$ is the imaging lens, whereby the image lens $L_2$ serves to form the image of the objective lens $L_1$ on the film again. M is a quick return mirror for picking up the view finder light beam. A is the photographing aperture stop, arranged at a position conjugate with the pupil P with reference to the objective lens $L_1$ and corresponding to the focal plane at the object side, of the image forming lens $L_2$. When in this case the image in the air, of the object is focused by moving the film F and the mirror M at the same time along the direction of the optical axis and observing the image through the eye piece of the view finder, the dimension of the pupil through which the light beam, namely, the image of the aperture as seen from the film side does not change, while the eye piece is moved forwards or backwards during the focusing operation. Thus, the observer has to move his face forwards or backwards in order to follow the eye piece, which is inconvenient.

In FIG. 7, $L_3$ is the focusing lens, which is moved along the direction of the optical axis for focusing. In the case of the present instrument, it is possible to carry out focusing without moving the face, while along with the movement of the lens $L_3$, the position of the pupil through which the light beam changes and at the same time the dimension of the pupil also changes so that the magnification factor as well as the light amount change.

SUMMARY OF THE INVENTION

A first purpose of the present invention is to carry out the focusing without changing the dimension of the pupil.

A second purpose of the present invention is to carry out focusing without changing the position of the pupil.

A third purpose of the present invention is to carry out focusing without moving the light detecting plane.

The focusing here includes not only the case where the object and the light detecting plane or the observation plane are continuously kept in conjugate relationship with each other but also the case where the both are momentarily brought into conjugate with each other.

BRIEF DESCRIPTION OF THE DRAWINGS

FIG. 1 shows the first embodiment in section.

FIG. 2 shows the first embodiment in section, whereby the object is in focus.

FIG. 3 shows the second embodiment in section.

FIG. 4 shows the third embodiment in section.

FIG. 5 shows the fourth embodiment in section.

DESCRIPTION OF THE PREFERRED EMBODIMENTS

Figure 6:
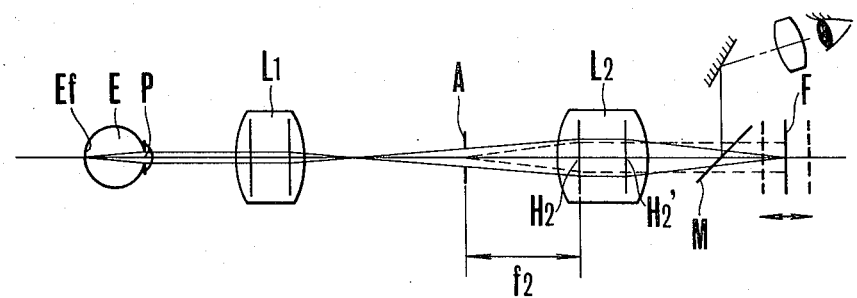
FIG. 6 shows conventional optics of the ophthalmic instrument.
Figure 7:
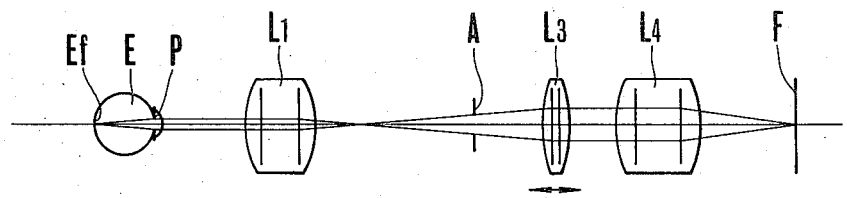
FIG. 7 shows another type of conventional optics of the ophthalmic instrument.

FIGS. 1 and 2 show an eye examining system in accordance with the present invention. In the drawing, E is the eye to be inspected, Ef is the eye fundus and P is pupil. Further, $L_1$ is the objective lens. $L_5$ is the positive intermediary lens, $H_5$ is its primary (front) principal plane, $H'_5$ is its secondary (rear) principal plane and $f_5$ is the front focal length. A is the aperture stop, which is fixed on the front focal plane of the intermediary lens $L_5$. F is a light detecting plane such as provided by photoelectric cells or photographic film, while $L_6$ and $L_7$ from respectively a positive movable lens, which moves along the direction of the optical axis. $H_6$ is the front principal plane of the lens $L_6$ while $H'_6$ is the rear principal plane. $H_7$ is the front principal plane of the lens $L_7$, while $H'_7$ is the rear principal plane. Further $f_6$ is the rear focal length of the lens $L_6$, while $f_7$ is the front focal length of the lens $L_7$. Hereby, each of the lenses $L_1$, $L_5$, $L_6$ and $L_7$ may consist of a plural number of element lenses in practice.

The distance between the movable lenses $L_6$ and $L_7$ is determined in such a manner that the distance between the rear principal plane $H'_6$ of the lens $L_6$ and the front principal plane $H_7$ of the lens $L_7$ is equal to the sum of their focal lengths $(f_6+f_7)$, whereby the lenses $L_6$ and $L_7$ are secured on the lens barrel, not shown in the drawing, so that the distance between both lenses can not vary. Hereinafter, such are called movable lens groups inclusive of the lenses $L_6$ and $L_7$.

When the distance between the lenses $L_6$ and $L_7$ is determined in the above mentioned way, the movable lens group constitutes an afocal system, so that the parallel rays incident upon the movable lens group go out of the lens group parallel. Further, if the point light source is placed at the center of the aperture A, the rays having passed through the intermediary lens $L_5$ go out of the lens parallel, so that even when the movable lens group is moved, the position and the dimension of the pupil through which the rays go out are kept constant.

The light beam $l_1$ shown in a rigid line in FIG. 1 shows the principal ray, while the light beam $l_2$ shown in a broken line shows the beam along the optical axis. The light beam from the eye fundus Ef goes out of the eye E to be inspected, condensed once by means of the objective lens $L_1$ and then diverged in such a manner that the intermediary image is further formed on the light detecting plane F by means of the lenses $L_5$ and $L_6$. Further, in the case of the eye examining system, an apertured mirror for guiding the illumination light is conventionally provided obliquely nearly at the position of the aperture A.

In order that the eye E' (FIG. 2) to be inspected and having a refractive error be in focus, the movable lens group $(L_6, L_7)$ is moved, for example, forwards by a distance X out of the position at which the ideal eye E shown in FIG. 1 is in focus.

Hereby, the diopter amount D of the eye to be inspected and the displacement amount X of the movable lens group from the position at which the ideal eye is in focus to the position at which the eye to be inspected is in focus is represented as follows.

$$X = \frac{(f_5)^2 (f_7)^2}{100\{(f_6)^2 - (f_7)^2\}} D$$

(Hereby, $f_5$, $f_6$ and $f_7$ are respectively the focal length of the lenses $L_5$, $L_6$ and $L_7$.)

As can be understood from the above relation, the variation of the diopter amount has a linear relation to the displacement amount of the lens group so that the cam for moving the lens to the diopter amount carries out a linear movement, which is convenient for displaying the diopter amount as in the case of the ophthalmic instrument such as an eye refractometer. Hereby, in the case of the ophthalmic instrument, the pupil P is in conjugate relationship with the aperture A with reference to the lens $L_1$.

FIG. 3 shows another embodiment, whereby the lenses $L_1$, $L_5$, $L_6$ and $L_7$ have the same efficiency as in the case shown in FIG. 1. Hereby, the aperture A is arranged at the position corresponding to the rear focal plane of the movable lens $L_5$ and the front focal plane of the movable lens $L_6$ so as to be movable along with the movable lenses $L_5$ and $L_6$. Being arranged in this way, the aperture A is conjugated with the front focal plane A' of the intermediary lens $L_5$ so that same effect as the case shown in FIG. 1 can be obtained.

FIG. 4 shows further another embodiment. In the drawing, the objective lens $L_1$, the intermediary lens $L_5$ and the aperture A are the same as those in FIG. 1, while the movable lens group consists of a negative lens $L_8$ and a positive lens $L_9$. $H_8$ is the front principal plane of the negative lens $L_8$, $H'_8$ is the rear principal plane and $f_8$ is the focal length. $H_9$ is the front principal plane of the positive lens $L_9$, $H'_9$ is the rear principal plane and $f_9$ is the focal length. Hereby, the lenses $L_8$ and $L_9$ are fixed in the lens barrel, not shown in the drawing, in such a manner that the front focal plane of the negative lens $L_8$ corresponds to the front focal plane of the positive lens $L_9$, so that the lenses $L_8$ and $L_9$ constitute an afocal reverse Galilean telephoto system. Also in this case, the principal ray passing through the center of the aperture A is directed parallel to the optical axis by means of the intermediary lens $L_5$, so that even if the afocal movable lens group ($L_8$, $L_9$) is moved, the principal ray incident upon the photographing plane F is parallel to the optical axis while the incident height is also constant.

FIG. 5 shows yet another embodiment. Hereby, the movable lens group constitutes an afocal Galilean telephoto system in which the positive lens $L_{10}$ at the object side and the negative lens $L_{11}$ at the image side are arranged in such a manner that the rear focal plane of the positive lens $L_{10}$ corresponds to the rear focal plane of the negative lens $L_{11}$. Also in this case, the position and the dimension of the pupil through which the light goes out remains unchanged even if the movable lens group ($L_{10}$, $L_{11}$) is moved along the direction of the optical axis. In the case of the above mentioned embodiments, the present invention has been explained in accordance with the application in the field of the ophthalmic system so that the light beam going out of the objective lens is once converged and reaches the aperture. On the other hand, in the case of the application in the field of the photographing lens, it is not necessary to form an image on the way while further the lens corresponding to the objective lens can be eliminated, that is, the front diaphragm optical system is sufficient.

In accordance with the present invention, even if the lens group is moved for focusing, the position of the pupil remains unchanged so that the magnification factor is not changed while the light amount is not changed. Consequently, in accordance with the conventional instrument, when the refractive power of the respective eye to be inspected differs from each other, the photographing magnification power as well as the exposure condition differ depending upon the position of the focusing lens, which is inconvenient for the comparison and the inspection. However, in accordance with the present invention, the above difficulties can be advantageously eliminated. Further, the same efficiency can be obtained also for the ordinary photographing.

What is claimed is:

1. An optical system with a focusing group comprising:
    a fixed lens for substantially collimating the principal rays;
    an aperture stop; and
    a movable lens group consisting of a plural number of lenses for constituting an afocal optical system for the whole movement range, movable along the direction for focusing and arranged at the image side of the fixed lens.

2. An optical system in accordance with claim 1, wherein the aperture stop is arranged on the front focal plane of the fixed lens.

3. An optical system in accordance with claim 1, wherein the aperture stop is movable together with the movable lens group.

4. An optical system in accordance with claim 1, wherein an objective means is provided before the fixed lens.

5. An optical system in accordance with claim 1, wherein the movable lens group consists of two positive lens means whose focal planes coincide with each other.

6. An optical system in accordance with claim 1, wherein the movable lens group consists of a positive and a negative lens means whose focal planes coincide with each other.

7. An optical system with a focusing group comprising:
    a fixed lens;
    a focusing lens group being arranged behind the fixed lens, movable along the direction of the optical axis and consisting of two lens means whose focal planes correspond to each other; and
    aperture means being arranged so as to substantially coincide with the focal plane and movable, making one body with the focusing lens group.

8. An optical system in accordance with claim 7, wherein an objective means is arranged before the fixed lens.

9. An optical system comprising:
    objective means for imaging the light flux from the fundus of an eye to be inspected;
    fixed lens means positioned at the image side of said objective means;

aperture means substantially positioned at the primary focal plane of said fixed lens means for limiting the light flux; and a focusing lens group arranged behind said fixed lens means, movable along the optical axis and substantially afocal with respect to the anterior part of the eye to be inspected.

10. An optical system in accordance with claim 9, further including a diaphragm which is arranged within said focusing lens group.

11. An optical system in accordance with claim 9, wherein said focusing lens group consists of two positive lens means whose focal planes coincide with each other.

12. An optical system in accordance with claim 9, wherein said focusing lens group consists of positive and negative lens means whose focal planes coincide with each other.

13. An optical system in accordance with claim 9, wherein said aperture means is arranged at a position conjugate with the anterior part of the eye to be inspected.

* * * * *